United States Patent [19]

Moorehead

[11] Patent Number: 4,983,168
[45] Date of Patent: Jan. 8, 1991

[54] MEDICAL LAYERED PEEL AWAY SHEATH AND METHODS

[75] Inventor: Harvey R. Moorehead, Salt Lake City, Utah

[73] Assignee: Catheter Technology Corporation, Salt Lake City, Utah

[21] Appl. No.: 295,076

[22] Filed: Jan. 5, 1989

[51] Int. Cl.[5] .............................................. A61M 5/178
[52] U.S. Cl. ..................................... 604/161; 604/280
[58] Field of Search ................................ 604/158-170, 604/280, 171, 264

[56] References Cited

U.S. PATENT DOCUMENTS

| | | | |
|---|---|---|---|
| Re. 31,855 | 3/1985 | Osborne | 604/161 |
| 2,227,682 | 1/1941 | Wade | 18/57 |
| 3,382,872 | 6/1965 | Rubin | 604/164 |
| 3,656,479 | 4/1972 | Huggins | 128/214.4 |
| 3,677,243 | 7/1972 | Nerz | 604/161 |
| 4,166,469 | 9/1979 | Littleford | 128/347 |
| 4,182,582 | 1/1980 | Youval et al. | 405/45 |
| 4,243,050 | 1/1981 | Littleford | 128/347 |
| 4,306,562 | 12/1981 | Osborne | 604/164 |
| 4,345,606 | 8/1982 | Littleford | 128/784 |
| 4,354,491 | 11/1982 | Marbry | 604/161 |
| 4,402,685 | 9/1983 | Bühler et al. | 604/280 |
| 4,411,654 | 10/1983 | Boarini et al. | 604/161 |
| 4,412,832 | 11/1983 | King et al. | 604/161 |
| 4,451,256 | 5/1984 | Weiki et al. | 604/164 |
| 4,596,559 | 6/1986 | Fleischhacker | 604/170 |
| 4,723,942 | 2/1988 | Scott | 604/161 |
| 4,747,833 | 5/1988 | Kousai et al. | 604/164 |
| 4,772,266 | 9/1988 | Groshong | 604/160 |
| 4,776,846 | 10/1988 | Wells | 604/161 |
| 4,781,690 | 11/1988 | Ishida et al. | 604/164 |
| 4,830,805 | 5/1989 | Kousai et al. | 264/209 |

FOREIGN PATENT DOCUMENTS

| | | |
|---|---|---|
| 021446 | 1/1981 | European Pat. Off. . |
| 245837 | 11/1987 | European Pat. Off. . |
| 286108 | 10/1988 | European Pat. Off. . |
| 3635695C1 | 9/1987 | Fed. Rep. of Germany . |

*Primary Examiner*—Stephen C. Pellegrino
*Assistant Examiner*—Kathleen A. Daley
*Attorney, Agent, or Firm*—Workman Nydegger Jensen

[57] ABSTRACT

A layered peel away hollow sheath for temporarily creating a passageway into a desired body site of a medical patient for placement of one end of an indwelling device at the body site through the sheath, the sheath wall comprising at least two layers, the inside layer being cylindrical and the outside layer comprising two semi-cylindrical segments defining opposed axially-directed slits or slots therebetween which comprises tear lines such that the sheath manually tears axially along the single layer tear lines into two pieces for removal of the sheath from around the indwelling device.

11 Claims, 1 Drawing Sheet

MEDICAL LAYERED PEEL AWAY SHEATH AND METHODS

FIELD OF THE INVENTION

The present invention relates generally to a medical peel away sheath, and related methods, and more particularly to a novel layered peel away sheath intended to temporarily preserve a tubular passageway from the exterior to a desired interior body site or internally between two body sites.

BACKGROUND AND PRIOR ART

For many medical purposes, it is important to place devices, including soft, yielding devices, through the skin and underlying tissue layers and into blood vessels or other compartments or locations inside the body of a medical patient. These include but are not limited to catheters, pacemaker leads and hydrocephalic shunts. Such devices often have one end in the desired location or compartment and the other outside the body, i.e. they are transcutaneous devices because they cross the skin during placement and/or in use. Identical problems occur placing devices from one compartment to another within the body, e.g. placing a catheter from the subcutaneous tissue area into the blood vessel when the catheter is to be used in conjunction with a subcutaneous vascular access portal. Transcutaneous devices are included when the term intercompartmental is used herein. Several methods have been used to place such devices, each with advantages and problems.

Perhaps the earliest and most straight forward approach is to surgically cut an opening through from one compartment into the other compartment, insert the device, then sew up the surgical wound which will self-repair and heal around the device. One example of this is known as the "cut-down" placement of a catheter. In this procedure, the physician cuts through the skin with a scalpel down to a blood vessel, nicks the vessel, inserts the catheter tip through the nick and into the vessel, advances the catheter tip to the desired location, sews the vessel wall tightly around the catheter, and finally sews up the skin incision. One advantage of this method is that generally any device can be placed practically anywhere in the body. Disadvantages include the need for a skilled, highly trained physician as well as specialized medical facilities to perform the procedure safely, and the trauma, disruption and infection risk to the many tissues involved.

To address these disadvantages, percutaneous methods have been developed to create small openings and place such devices through them with minimal tissue disruption, using specialized placement assist devices to reduce the need for skilled personnel and elaborate operating room facilities. One such device is a solid dilator. The key features include a tapered end which will spread aside the tissues at a puncture site as the dilator is advanced through tissue from one compartment to another compartment and a hollow interior passage through which the device can be advanced once the dilator has created the opening. The dilator is then removed over the end of the device. A succession of gradually larger-sized dilators are sometimes used to create a large hole through which a relatively large device can be inserted. If the device is sufficiently firm, stiff and unyielding, the dilator may be used to prespread the tissue and create the opening, then withdrawn completely and the stiff device quickly inserted through the opening thus created before it has a chance to reclose.

However, many medical devices, including pacer leads, catheters and hydrocephalic shunts, must be made extremely soft and supple or else they will damage the body during long indwelling times resident in internal body compartments. Such devices, which are too soft and supple to respread such a predilated opening, must be inserted through the dilator or some other device which is stiffer. Such a device may be the one which has created the opening or it may be a second device which can hold open such a pre-dilated opening created in the tissue. However, the maximum diameter of the device to be placed can be no larger than the minimum diameter of the interior passage inside the solid dilator or other hold-open device because of the need to ultimately slide the dilator or hold-open device off over the device that is being placed.

This latter requirement poses a problem for many devices. For example, both catheters and pacemaker leads are devices which terminate (at the end outside the body) in connectors which, for effective use, need to be much larger than the device (catheter or lead) itself. Pacemaker leads may actually be pre-attached to the pacemaker. To place such a device with a solid dilator, the dilator must be made with an internal passageway as large as the largest part of the device, in this case, the terminating connector. This creates problems. The hole through the tissue must be much larger than that required to accommodate passage of a catheter tube or a pacemaker, creating tissue trauma and disruption. The required hole may be so big that it cannot be created by spreading or pushing aside the tissue, but can only be cut surgically with a scalpel, thus requiring a return to the technique less preferred. When the thin part of the device is advanced through the dilator, there will now be much empty space between the device and the walls of the internal passageway of the dilator, creating a pathway for unintended and undesirable fluids to pass between compartments during the placement procedure. One example of this could be an air embolism entering a blood vessel between a small catheter and an oversized dilator during a catheter placement procedure, a potentially life-threatening complication.

A device which solves this problem is a peel away sheath, often used in conjunction with a solid dilator. The peel away sheath is a very thin-walled, usually cylindrical device that is placed in position so that it provides a communicating passageway through the tissue. This is often accomplished by fitting the sheath tightly over a solid dilator, advancing both devices through the tissue together as a unit, then removing the solid dilator from inside the sheath, leaving the sheath alone in the desired position acting to hold the penetrated site in an open condition. Then the catheter tube or other instrument is advanced through the sheath into the desired position. The peel away sheath is capable of being readily and reliably pulled apart lengthwise into two pieces. This allows it to be made as small as the intercompartmental portion of the device, then removed by being pulled apart despite the presence of a (usually enlarged) connector or other end fitting. Proximal handles on the sheath are generally provided to facilitate grasping and tearing.

Two types of peel away sheaths are known in the prior art. U.S. Pat. No. Re 31,855, discloses a sheath, preferably of polytetraflourethylene material, that has an internal molecular orientation which tears easily in a lengthwise direction and with great difficulty in crosswise or oblique directions. This prevents an incomplete lengthwise tear which would result in an inability to remove the sheath. This sheath is furnished to the user already provided with pre-started, diametrically opposed longitudinal proximal tears. This sheath has the advantage of producing reliable tears. The tearing motion itself is easily performed by hand without the aid of a mechanical tearing device, is easily controlled, and has a good, smooth "feel" in use. Disadvantages include the severe limitation imposed on the materials that may be used for construction, whiCh can only be materials capable of being fabricated with an oriented molecular structure. This makes it difficult to reliably attach handles, difficult to consistently fabricate a well-tapered tip to facilitate advancing the sheath through the tissue over the dilator, and difficult for the sheath to resist kinking when the sheath cylinder is bent while in use.

U.S. Pat. Nos. 4,166,469, 4,243,050 and 4,345,606 disclose a sheath longitudinally scored or perforated on opposite sides. The result is a cylindrical sheath with two weakened lines which run lengthwise on opposite sides of the cylinder. It relies for its operation on the thinned, scored or perforated regions being mechanically weakened and, therefore, less resistant to tearing than the rest of the sheath cylinder, causing the tear, once started, to propagate along the weakened region and hence in a lengthwise fashion only. Advantages include a broader selection of materials permitting somewhat easier handle attachment, easier tip fabrication and better kink resistance. However, the same material is still used throughout, thus requiring that the material selected to fabricate the sheath possess properties which are a compromise between the above-mentioned factors and longitudinal shear strength. Other disadvantages also include the difficulty of consistently fabricating a sufficiently weakened area to produce 100% consistent tears, less well-controlled and smooth tears and tears that have poorer "feel".

BRIEF SUMMARY AND OBJECTS OF THE INVENTION

The present invention overcomes or substantially alleviates the aforestated problems and, in brief summary, comprises a layered peel away hollow sheath for temporarily creating a passageway into a desired body site of a medical patient for placement of one end of an indwelling instrument at the body site through the sheath. The sheath comprises a tube having a proximal end and a distal end comprising synthetic resinous material, the sheath comprising a wall comprising at least two layers as well as an outside surface and an inside surface defining a hollow interior. The outside layer is interrupted by a longitudinally directed slit or narrow slot on opposite sides of the sheath. In other words, the inside layer typically comprises a cylinder and the outside layer two opposed semi-cylinders integrally with the inside layer but spaced from each other so as to define two opposed axially-extending slits or slots which comprise weaker tear lines. The sheath also comprises opposed first and second grasping structures carried by the remainder wall at the proximal end of the tube whereby, when the grasping structures are pulled apart, the tube tears axially along the two single layer tear lines into two pieces.

In its preferred form, the tube of the sheath is cylindrical, and may be formed in any suitable way. The outer layer may initially comprise two semi-cylinders fabricated by extrusion or injection molding the inside surfaces of which are joined by bonding, welding or in any other satisfactory way adhered to the outside surface of the inside cylindrical layer. Alternatively, the outside layer segments can be formed by extrusion in which the extrusion die first forms the inside cylindrical layer and then extrudes the outer semi-cylindrical segments upon the cylindrical layer.

Additionally, the two layers may be the same basic plastic with or without one or more appropriate additives.

Conversely, the material used to form the inside cylindrical layer may be much weaker in shear than the material used to form the outside layer segments.

The layers may be colored differently.

With the foregoing in mind, it is a primary object of the invention to provide a novel layered axially severable or peel away sheath, and related methods, for creating a passageway into a desired medical patient body site for placing an indwelling instrument therethrough.

It is another significant object to provide a novel medical sheath comprising at least two wall layers wherein two opposed axial slits or slots exist in the outer layer to accommodate facile tearing of the sheath into two pieces while still surrounding an indwelling instrument placed through the sheath.

These and other objects and features of the present invention will be apparent from the detailed description taken with reference to the accompanying drawings.

DETAILED DESCRIPTION OF THE ILLUSTRATED EMBODIMENT

Figure 1:
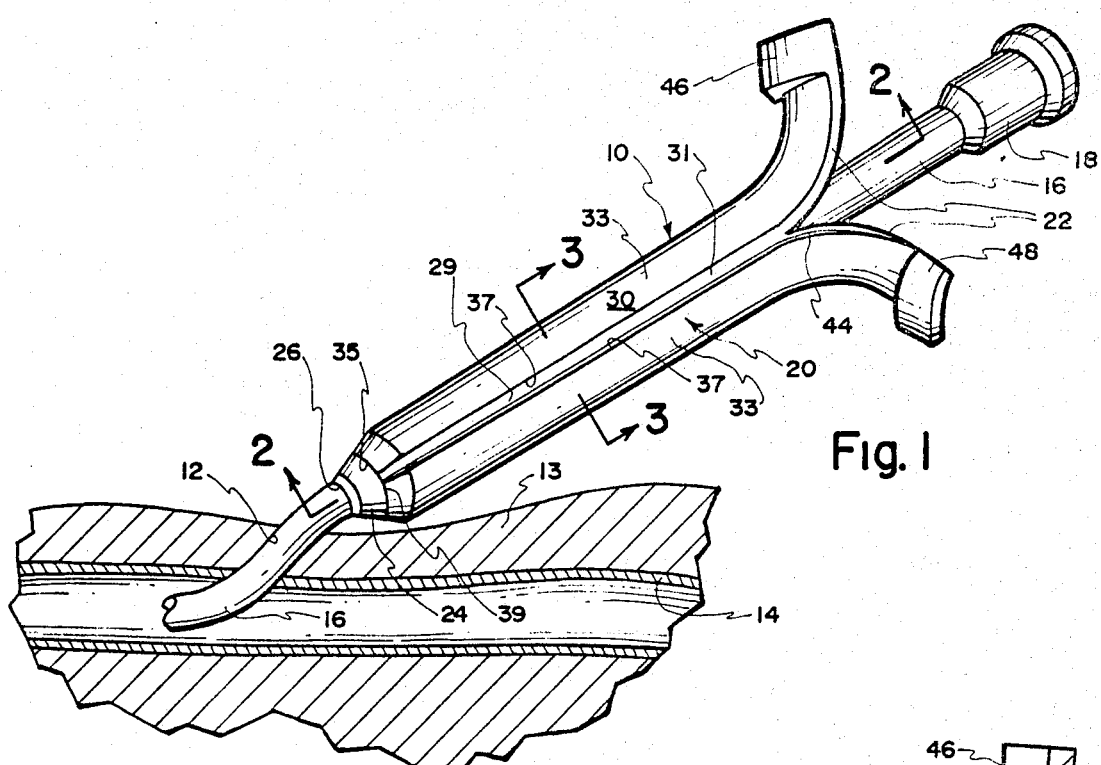
FIG. 1 is a perspective representation with portions broken away for clarity, of a sheath, embodying the features of the present invention, being used to place a catheter tube in the vein of a patient.
Figure 2:
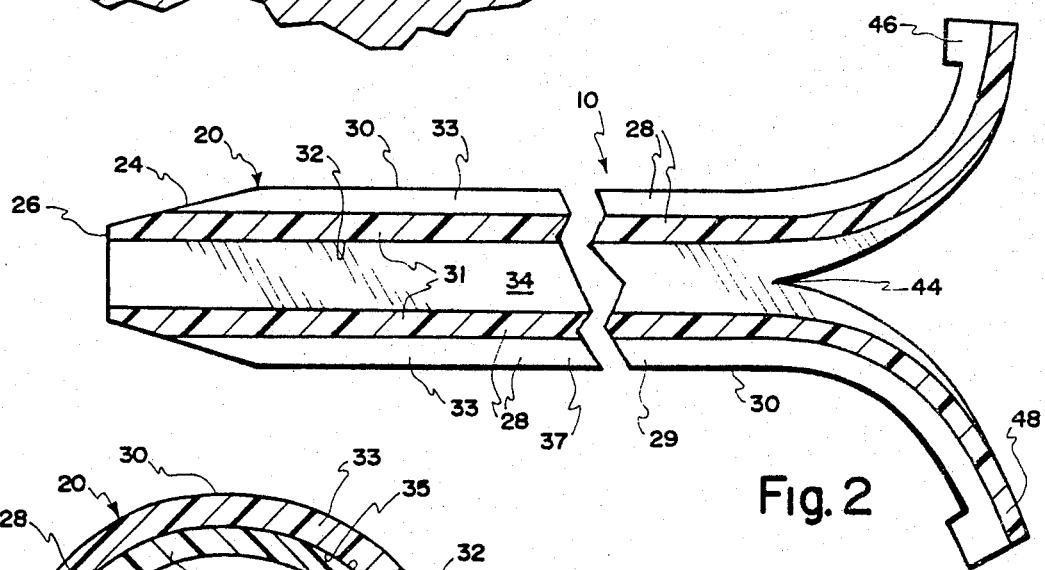
FIG. 2 is an enlarged cross-section taken along lines 2—2 of FIG. 1.
Figure 3:
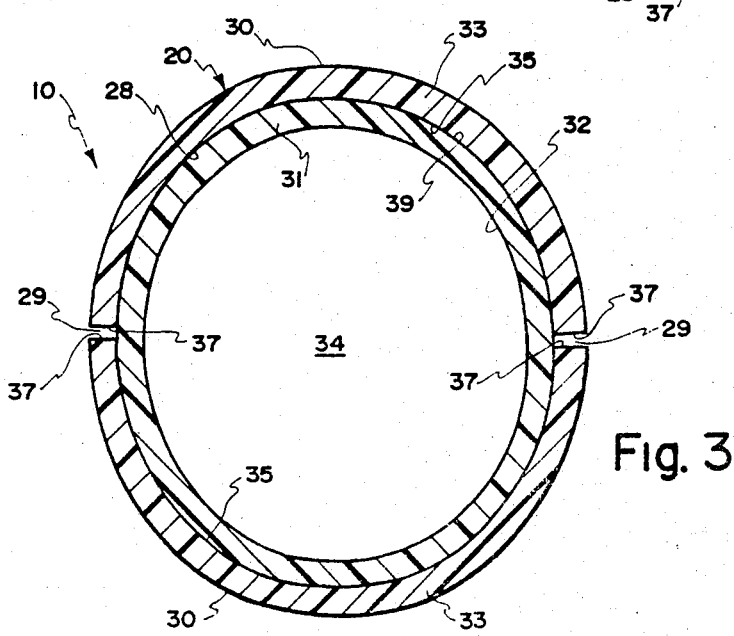
FIG. 3 is an enlarged cross-section taken along lines 3—3 of FIG. 1.

Reference is now made to the drawings, wherein like numerals are used to designate like parts throughout. FIGS. 1 through 3 illustrate a presently preferred medical peel away sheath, generally designated 10, fashioned in accordance with the principles of the present invention. Peel away sheath 10 comprises an integral layered device intended to temporarily preserve a tubular passageway from the exterior to a desired body site or internally between two body sites of a medical patient. Peel away sheath 10 is illustrated as having been retracted from a penetration site 12 from the exterior to a desired body site, i.e. through subcutaneous tissue 13 into a cardiovascular vein 14, where the sheath 10 earlier temporarily preserved a tubular passageway (the hollow interior of the sheath) at penetration site 12 while a pliant catheter tube 16 was inserted into the vein 14 through the hollow interior of the peel away sheath 10.

Retraction of the peel away sheath 10 to the position illustrated in FIG. 1 is preliminary to severing the sheath 10 into two parts for removal of the same transversely from the catheter tube 16 thereby avoiding telescopic retraction over the proximal hub 18 at the trailing end of the catheter tube.

Typically, catheter tubes of the type used in conjunction with peel away sheaths are extremely soft and supple, having insufficient strength to be placed in a vein or the like using techniques which impose force upon the catheter tube. Such catheter tubes are often formed of silicone rubber or equivalent, which is extremely compatible with human and animal tissue.

Notwithstanding the foregoing, it is to be appreciated that peel away sheaths of the type under consideration may be used not only to access to a desired body site from the exterior of a medical patient, but to access between two internal body sites.

The sheath 10 generally comprises a layered tube 20 having a proximal end 22 and a distal end 24. Distal end 24 is illustrated as being in the form of a tapered tip having an axial port 26, the inside diameter of which is substantially the same as the outside diameter of the catheter tube 16. Other tip configurations, of course, can be used.

The tube 20 is comprised of synthetic resins. The tube 20 also comprises a multi-layered wall 28 (FIG. 3), which is illustrated as having a uniform thickness except for opposed, axially directed slits or narrow slots 29. More specifically, multi-layered wall 28 comprises an interior cylindrical layer 31, shown as being of uniform thickness, and two exterior layer segments 33 of semi-cylindrical configuration, illustrated as being of uniform thickness. Each semi-cylindrical layer segment 33 comprises an exterior surface 30 and interior interfaces 35 (where each layer segment 33 merges integrally with layer 31). Each layer segment 33 comprises axially-directed edges 37, which define slots or slits 29. The cylindrical layer 31 comprises interface 39 (where layer 31 integrally merges with layer segments 33). Layer 31 comprises an internal cylindrical surface 32, which defines hollow interior 34. Hollow interior 34 functions as a snug passageway for the catheter tube 16. The two semi-cylindrical layer segments 33, separated by slits 29, defines opposed axial tear lines along layer 31 adjacent slits 29.

The layer 31 comprises two opposed V-shaped tears 44 at the proximal end of the sheath 10. The opposed V-shaped tears 44 are interposed between opposed first and second grasping structure or handles 46 and 48. Notches 44 serve to aid in starting the peeling or tearing process, as hereinafter more fully described. Handles 46 and 48 are illustrated as being merely transverse flange-like enlargements of the semi-cylindrical wall portions 33. Once the peel away sheath 10 is in the position illustrated in FIG. 1, the user merely grasps the handles or grasping structure 46 and 48 and pulls outwardly and distally causing the layer 31 to propagate the notches 44 as opposed tears axially-directed along the two tear lines, created by the existence of slits 29, into two pieces thereby transversely removing the sheath 10 from a position circumscribing the indwelling catheter tube 16.

It is presently preferred that the peel away sheath 10 be extruded simultaneously or on a staggered basis from one or two different extrusion materials, following which the resulting tubing is cut into lengths and the tips 24, the notches 44 and handles 46 and 48 formed thereafter. For example, the semi-cylindrical layer segments 33 may comprise polyethylene or Teflon and the segments 31 highly plasticized polyurethane. High density polypropylene or polyurethane may comprise semi-cylindrical layer segments 33 and low density polypropylene or polyurethane may comprise the interior layer 31.

Alternatively, semi-cylindrical layer segments 33 can be fabricated by extrusion or injection molding and later joined by bonding, welding or the like to the interior layer 31.

The two materials may also be the same basic synthetic resinous material, but modified with certain additives. The additive, placed in the interior layer 31 can be a filler. The relative strengths of various synthetic resinous materials are well known in the art as are the effect of additives on strength. Calcium carbonate or talc added to most applicable synthetic resinous materials, including polypropylene, in an amount of about 30% or more up to about 75% by weight may be used to produce the interior layer 31 or that portion of layer 31 adjacent the slits 29 and in an amount from 1% to about 20% by weight may be used to produce strengthened semi-cylindrical layer segments 33. Barium can be added to the material used to form any layer. If added to layer 31 in a range of 30-75 percent by weight, the layer 31 is made substantially weaker than the same material without the barium. At the same time, barium provides the resulting device with radiopacity. Fiberglass and/or glass beads may be added to strengthen the semi-cylindrical layer segments 33.

Conventional technology may be used to color code the various layers, if desired.

The invention may be embodied in other specific forms without department from the spirit or essential characteristics thereof. The present embodiment, is, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. A peel away hollow sheath for temporarily creating a passageway into a desired body site of a medical patient for placement of one end of an indwelling device at the body site through the sheath, the sheath comprising:

a laterally continuous conduit having an interior surface forming a hollow borehole therethrough and an exterior surface;

at least one exterior layer segment securely attached about a substantial portion of the exterior surface of the laterally continuous conduit such that the integral strength of the laterally continuous conduit is not weakened by the at least one exterior layer segment and such that at least one longitudinal axially-directed slot is formed where said at least one exterior layer segment is unattached to the exterior surface of the laterally continuous conduit; and opposed first and second grasping means adjacent a proximal end of the at least one exterior layer segment whereby when the grasping means are manually pulled apart the laterally continuous conduit tears longitudinally adjacent the axially directed slot formed where the at least one exterior layer segment is unattached to the exterior surface of the laterally continuous conduit.

2. A peel away sheath according to claim 1 wherein the laterally continuous conduit and the at least one exterior layer segment comprise an identical synthetic resinous material.

3. A peel away sheath according to claim 1 wherein the laterally continuous conduit and the at least one exterior layer segment are cylindrically shaped.

4. A peel away sheath according to claim 1 wherein the laterally continuous conduit and the at least one exterior layer segment are co-extruded simultaneously.

5. A peel away sheath according to claim 1 wherein the at least one exterior layer segment is formed separate from but later integrally joined to the laterally continuous conduit.

6. A peel away sheath according to claim 1 wherein the wall means are selectively color coded.

7. A peel away sheath for temporarily creating a passageway into a desired body site of a medical patient for placement of one end of an indwelling device at the body site through the sheath, the sheath comprising:
  tube means of synthetic resinous material having a proximal end and a distal end and comprising layered wall means comprising an outside surface and an inside surface defining a hollow interior, said layered wall means comprising a laterally continuous interior layer and exterior layer segments defining opposed longitudinally disposed axially-directed slot means, capable of defining tear lines on the outside surface of said tube means, the interior layer comprising a first synthetic resinous material and the exterior layer segments comprising a second synthetic resinous material; and
  opposed first and second grasping means at the proximal end of the tube means, such that when the grasping means are manually pulled apart the tube means tears into two pieces axially along the tear lines at the slot means.

8. A peel away sheath for temporarily creating a passageway into a desired body site of a medical patient for placement of one end of an indwelling device at the body site through the sheath, the sheath comprising:
  tube means of synthetic resinous material having a proximal end and a distal end and comprising layered wall means comprising an outside surface and an inside surface defining a hollow interior, said layered wall means comprising a laterally continuous interior layer and exterior layer segments defining opposed axially-directed slot means capable of defining tear lines on the outside surface of said tube means, the material comprising the exterior layer segments and the material comprising the interior layer differ one from the other by additive means; and
  opposed first and second grasping means at the proximal end of the tube means, such that when the grasping means are manually pulled apart the tube means tears into two pieces axially along the tear lines at the slot means.

9. A peel away sheath according to claim 8 wherein the additive means comprise filler means placed in the material from which the interior layer is formed.

10. A peel away sheath according to claim 8 wherein the additive means comprise radiopaquing means placed in one of said two materials.

11. A peel away hollow sheath for temporarily creating a passageway into a desired body site of a medical patient for placement of one end of an indwelling device at the body side through the sheath, the sheath comprising:
  tube means of synthetic resinous material having a proximal end and a distal end and comprising a multi-layered wall means having a laterally continuous conduit having an exterior surface and an interior surface defining a hollow borehole, said layered wall means further having exterior layer segments securely attached to the exterior surface of said conduit such that the integral strength of the laterally continuous conduit is not weakened by the exterior layer segments and such that the exterior layer segments define opposed axially-directed slots; and
  opposed first and second grasping means adjacent a proximal end of the exterior layer segments such that when the grasping means are manually pulled apart the laterally continuous conduit tears longitudinally adjacent the axially directed slots formed where the exterior layer segments are unattached to the exterior surface of the laterally continuous conduit.

* * * * *

UNITED STATES PATENT AND TRADEMARK OFFICE
CERTIFICATE OF CORRECTION

PATENT NO. : 4,983,168

DATED : January 8, 1991

INVENTOR(S) : HARVEY R. MOOREHEAD

It is certified that error appears in the above-identified patent and that said Letters Patent is hereby corrected as shown below:

```
Column 2, line 25, "sOlid" should be --solid--
Column 3, line 13, "whiCh" should be --which--
Column 6, line 28, "department" should be --departing--
```

Signed and Sealed this

Tenth Day of November, 1992

*Attest:*

DOUGLAS B. COMER

*Attesting Officer*     Acting Commissioner of Patents and Trademarks